US00PP08043P

United States Patent [19]

van der Knaap

[11] Patent Number: Plant 8,043

[45] Date of Patent: Nov. 24, 1992

[54] CHRYSANTHEMUM PLANT—TOWN TALK CULTIVAR

[75] Inventor: Jacques C. M. van der Knaap, De Lier, Netherlands

[73] Assignee: Fides Beheer B.V., De Lier, Netherlands

[21] Appl. No.: 679,527

[22] Filed: Apr. 2, 1991

[51] Int. Cl.[5] ..... A01H 5/00

[52] U.S. Cl. ..... Plt./82.2

[58] Field of Search ..... Plt./74.1, 82.2, 74

*Primary Examiner*—Howard J. Locker

*Attorney, Agent, or Firm*—Burns, Doane, Swecker & Mathis

[57] ABSTRACT

A new and distinct cultivar of Chrysanthemum plant named Town Talk is provided. The new cultivar was the result of a controlled breeding program wherein the Fanfare cultivar (non-patented in the United States) was pollinated by the Lucky Strike cultivar (U.S. Plant Pat. No. 6,333). More specifically, the new cultivar forms attractive large yellow single flowers having a green center when immature. The inflorescence tends to be somewhat pyramidal in configuration. The response period of the flowers is approximately nine weeks. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously *Chrysanthemum morifolium*, Ramat., and hereinafter is referred to by the cultivar name Town Talk.

The new cultivar is the product of a planned breeding program which had as its objective the creation of a new Chrysanthemum cultivar which exhibits attractive yellow single flowers having a green center when immature, exhibits a flower response period of approximately nine weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1984 at De Lier, The Netherlands. The female parent (i.e., the seed parent) was to Fanfare cultivar (non-patented in the United States) and the male parent (i.e., the pollen parent) was the Lucky Strike cultivar (U.S. Plant Pat. No. 6,333). The parentage of the new cultivar can be summarized as follows:

Fanfare × Lucky Strike.

The seeds resulting from the above pollination were sown and plantlets were obtained which were physically and biologically different from each other. Selective study resulted in the identification of a single plant of the new variety.

It was found that the new cultivar of the present invention:

(a) exhibits attractive large yellow single flowers having an overall diameter of approximately 80 to 85 mm. wherein the disc florets are green in coloration when immature, (b) bears flowers in a somewhat pyramidal configuration, (c) exhibits a flower response period of approximately nine weeks, and (d) has the ability to produce flowers of commercially acceptable quality throughout the year in a cut mum production program.

Asexual reproduction of the new cultivar by cuttings initially taken during September, 1984, as performed at De Lier, The Netherlands, in a controlled environment has demonstrated that the characteristics of the new cultivar as herein disclosed are firmly fixed and are retained through successive generations of asexual propagation.

Town Talk has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Greta Verhagen cultivar (U.S. Plant Pat. No. 6,343), it is observed that the leaves tend to be larger, the vigor tends to be less, and the flower response tends to be slower. Otherwise, the flower type, the color of the ray florets, and the flower size tend to be substantially the same in each instance.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 10:00 a.m. to 12:00 noon under natural daylight conditions at De Lier, The Netherlands, during October, 1988. The plants described were grown under standard greenhouse conditions which approximate those commonly utilized for the production of cut mums.

Classification:

*Botanical.*—*Dendranthema morifolium* Ramat., cv. Town Talk.

*Commercial*—Cut single spray.

Inflorescence

A. Capitulum:

*Form.*—Pyramidal.

*Type.*—Single.

*Diameter across face.*—Approximately 80 to 85 mm. on average.

*Diameter of disc.*—Approximately 15-20 mm. on average.

B. Corolla of ray and disc florets:

*Color* (*General tonality from a distance of three meters.*)—Yellow.

*Color ray florets*(*top surface*).—Yellow Group 6B.

*Color disc florets.*—Yellow-Green Group 144B when immature changing to yellow when mature.

C. Reproductive organs:

*Androecium.*—Present in disc florets.

*Gynoecium.*—Present in both disc florets and ray florets.

Plant

A. General appearance:

*Height.*—Approximately 120 cm. on average.

B. Foliage:

*Coilor* (*upper surface*).—Yellow-Green Group 147A.

*Color* (*under surface*).—Yellow-Green Group 147B.

I claim:

1. A new and distinct cultivar of Chrysanthemum plant named Town Talk, substantially as herein shown and described, which:

(a) exhibits attractive large yellow single flowers having an overall diameter of approximately 80 to 85 mm. wherein the disc florets are green in coloration when immature, (b) bears flowers in a somewhat pyramidal configuration, (c) exhibits a flower response period of approximately nine weeks, and (d) has the ability to produce flowers of commercially acceptable quality throughout the year in a cut mum production program.

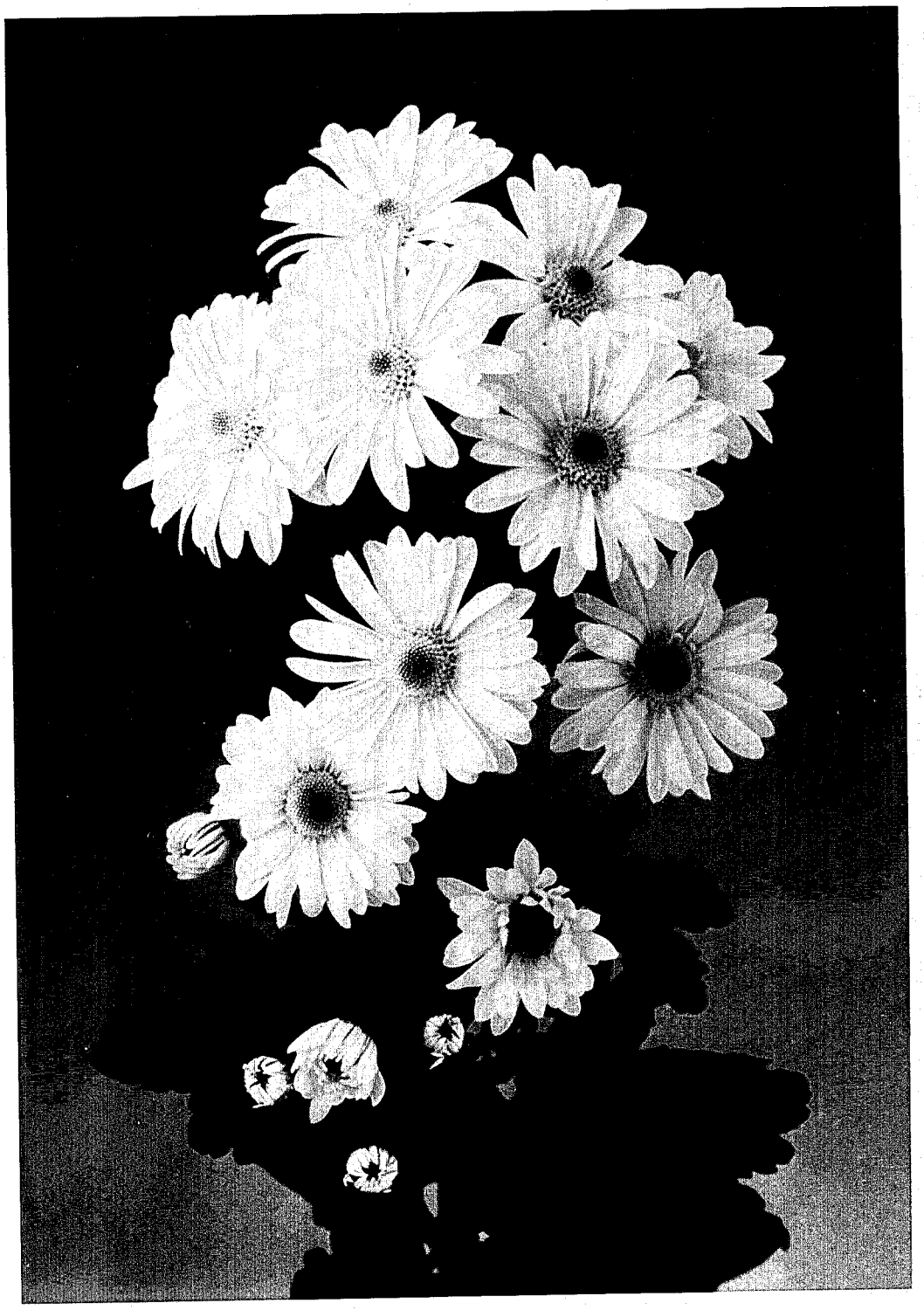

* * * * *